United States Patent [19]
Lemieux et al.

[11] Patent Number: 4,794,176
[45] Date of Patent: Dec. 27, 1988

[54] SYNTHESIS OF TUMOR ANTIGENIC DETERMINANT

[75] Inventors: Raymond U. Lemieux; Robert M. Ratcliffe, both of Edmonton, Canada; Donald A. Baker, Castro Valley, Calif.

[73] Assignee: Chembiomed, Edmonton, Canada

[21] Appl. No.: 918,935

[22] Filed: Oct. 15, 1986

Related U.S. Application Data

[63] Continuation of Ser. No. 277,680, Jun. 26, 1981, abandoned.

[51] Int. Cl.$^4$ ............... C07H 11/02; C07H 13/06
[52] U.S. Cl. .................................. 536/53; 514/23
[58] Field of Search ....................................... 536/53

[56] References Cited

U.S. PATENT DOCUMENTS 4,137,401  1/1979  Lemieux et al. .............. 536/53
4,195,174  3/1980  Lemieux et al. .............. 536/53

OTHER PUBLICATIONS

Kaifu and Osawa, Carbohydrate Res., 58:235–39 (1977) Elsevier Scientific Publishing Co., Amsterdam, Netherlands.
Kaifu and Osawa, Carbohydrate Res., 69:79–88 (1979) Elsevier Scientific Publishing Co., Amsterdam, Netherlands.
Bochkov and Zaikov, Chemistry of the O-Glycosidic Bond, 51–78 (1979).
Lemieux and Ratcliffe, Can. J. Chem., 57:1244 (1979).
Paulsen, Angewandte Chemie, Intl. Ed., 21:155 (1982).
Hoppner, et al., Vox Sang., 48:246 (1985).
Hoppner, et al., Molecul. Immunol., 22:1341 (1985).
Ratcliffe et al., Carbohydrate Research, vol. 93, pp. 35–41, Elsevier Scientific Publishing Co., Amsterdam, Netherlands (1981).

*Primary Examiner*—Ronald W. Griffin
*Attorney, Agent, or Firm*—Iver P. Cooper

[57] ABSTRACT

Processes are provided for the synthesis of the human T-antigenic determinant 2-acetamido-2-deoxy-3-O-($\beta$-D-galactopyranosyl)-$\alpha$-D-galactopyranoside containing an $\alpha$-O-glycosidically linked bridging arm O—$(CH_2)_n$COR. The determinant is coupled to carrier molecules to form artifical T-antigens, and to insoluble supports to form T-immunoadsorbents. The artificial T-antigen is shown to elicit a delayed type hypersensitivity reaction as a diagnostic for the presence of cancer in humans.

4 Claims, 2 Drawing Sheets 3,4,6-tri-O-acetyl-2-azido-2-
deoxy-β-D-galactopyranosyl chloride 3,4,6-tri-O-acetyl-2-azido-2-
deoxy-α-D-galactopyranosyl bromide 8-methoxycarbonyloctyl-2-acetamido-
2-deoxy-α-D-galactopyranoside 8-methoxycarbonyloctyl-2-acetamido
4,6-O-benzylidene-2 deoxy-
α-D-galactopyranoside 8-methoxycarbonyloctyl-2-acetamido-4,6-O-benzylidene-
2-deoxy-3-O-(2,3,4,6-tetra-O-acetyl-β-D-
galactopyranosyl)-α-D-galactopyranoside

6   R = OCH₃

8-methoxycarbonylotyl-2-acetamido-2-deoxy-
3-O-(β-D-galactopyranosyl)-α-D-galactopyranoside

7  R = NHNH₂

8  R = OH

SYNTHESIS OF TUMOR ANTIGENIC DETERMINANT

This application is a continuation of Ser. No. 277,680, filed June 26, 1981, now abandoned.

BACKGROUND OF THE INVENTION

The present invention relates to syntheses of the human T-antigenic determinant and antigens and immunoabsorbents formed therefrom.

Over fifty years ago, Thomsen[1] observed that human red cells, in vitro, could become transformed such that the cells became agglutinated by normal ABO compatible sera. After extensive investigation, Friedenreich[2] concluded that Thomsen's agent was a bacterial enzyme which degraded a natural antigenic determinant to liberate the so-called T receptor—a structure which is bound by an agglutinin of general occurrence in human sera. It is now established that the enzyme responsible for the transformation is a neuraminidase which exposed the T determinant by removing N-acetyl-α-D-neuraminidic acid residues (α-sialosides) from certain sialoglycoproteins[3].

In 1966, the structure of this determinant was shown by Kim and Uhlenbruck[4] to be the disaccharide βDGal(1→3)αDGalNAc which, in the glycoprotein, is glycosidically linked to a threonine or serine residue. The T-determinant is now known to occur in a wide variety of glycoproteins[5,6].

Recent findings that this structure occurs in tumor-associated antigens has caused a resurgence of interest in the investigation of this antigen and the corresponding antibodies. In particular, various investigators have shown that the T antigen can be demonstrated on tumor cells of animal and human origin[7-10]; that immediate and delayed type hypersensitivity reactions to the T antigen can be demonstrated in patients with certain forms of cancer[11]; and that changes in serum anti-T levels can be of diagnostic significance with regard to some cancers[11-12].

All of these observations have obvious important clinical implications both potential and realized. However, one major difficulty in developing the clinical applications is that prior to the present invention, the key component, a T antigen, was only available from natural sources chiefly through the laborious extraction of enzymatically treated human erythrocyte membranes[13]. This procedure affords only relatively small amounts of material which, because of its origin, is inherently difficult to purify and characterize. In addition, for applications such as delayed hypersensitivity testing in which T antigenic material is injected into humans, there is the added disadvantage that materials such as this, derived from human blood products, carry the risk of transmission of hepatitis.

The synthesis of a compound, O-β-D-galactopyranosyl-(1→3)-O-(2-acetamido-2-deoxy-α-D-galactopyranosyl)-N-Tosyl-L-serine, which contains the terminal disaccharide of the T-antigenic determinant, has been reported[14]. However, this compound was never demonstrated to have utility as the human T-antigenic determinant. It is not readily apparent whether the compound could be linked to an antigen-forming carrier molecule and further whether the resulting conjugate, if formed, would function as an artificial T-antigen. In fact it would be predicted that the unnatural highly antigenic N-tosyl group present in the aglycone moiety would cause antigens from this compound to be immunochemically dissimilar from the natural T-antigen.

In U.S. Pat. No. 4,137,401 issued to Lemieux, Bundle and Baker, a bridging arm is disclosed O-β-glycosidically linked to aldose moieties. The bridging arm has the structure O—R—COR'' where R is an aliphatic hydrocarbon moiety having 3–17 carbon atoms and R'' is H, OH, NH$_2$, NHNH$_2$, N$_3$ or a lower alkoxy group. The bridging arm enables one to link carbohydrate antigenic determinants to carrier molecules or solid supports to produce artificial antigens and immunoabsorbents. It should be appreciated that the reaction conditions set forth in the reference for attaching the bridging arm to the aldose moiety are those which will produce a β-D-anomeric glycosidic linkage. An α-D-anomeric bridging arm is desired in the T-anionic determinant.

In U.S. Pat. No. 4,195,174 issued Mar. 25, 1980, to Lemieux and Ratcliffe, processes are provided for the syntheses of O-acylated-2-azido-2-deoxy glycosyl halides. These halides can be converted to O-acylated-2-azido-2-deoxy glycosides. In particular the patent reports the synthesis of 3,4,6-tri-O-acetyl-2-azido-2-deoxy-β-D-galactopyranosyl chloride and its reaction with alcohols, including an aglycone bridging arm, to form 3,4,6-tri-O-acetyl-2-azido-2-deoxy-α-D-galactopyranosides.

SUMMARY OF THE INVENTION

As a solution to the problem of availability of T-antigenic material, we now wish to disclose a process which allows for the chemical synthesis of the T-antigenic determinant and thereby artificial T-antigens in large amounts. Of particular importance in the present invention is the demonstration that a synthesized artificial T-antigen can elicit a delayed type hypersensitivity (DTH) reaction diagnostic for the presence of cancer. This invention represents the first example of a hapten specific DTH response to an artificial antigen wherein the primary immunizing antigen was of natural origin.

In addition to the preparation of these artificial antigens, methodologies are also presented for the preparation of T-immunoadsorbents useful, for example, in the isolation of anti-T-antibodies.

In accordance with the process of the present invention, 3,4,6-tri-O-acyl-2-azido-2-deoxy-α-D-galactopyranosyl bromide is reacted with a monohydroxycarboxylate of the general formula HO(CH$_2$)$_n$COR where n=3–19 and R is an alkoxy or aryloxy protecting group, in the presence of R$_4'$NBr where R' is a lower alkyl group, in a suitable solvent. This product of this reaction is thereafter, in any order, reduced and N-acetylated to convert the azide group to an acetamido group (NHAc), and de-O-acylated, to produce an O-α-glycoside having the structure:

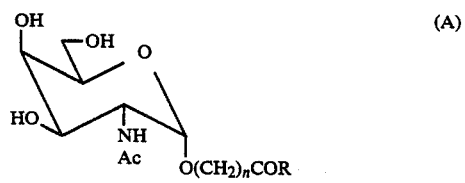

(A)

In accordance with another aspect of the present invention, the above O-α-glycoside is formed by reacting O-acylated-2-azido-2-deoxy-β-D-galactopyranosyl chloride with a monohydroxycarbonate of the general formula HO(CH$_2$)$_n$COR where n=3–19 and R is an alkoxy or aryloxy protecting group, in the presence of the promotor mercuric cyanide, in a suitable solvent. The product of this reaction is thereafter, in any order, reduced and N-acetylated to convert the azide group to an acetamido group, and de-O-acylated, to produce the above O-α-glycoside.

The O-α-glycoside is thereafter selectively blocked at the 4,6-O-positions and condensed with a 2,3,4,6-tetra-O-acyl-α-D-galactopyranosyl halide in the presence of a promoter, to form, after deblocking, the T-antigenic determinant hapten having the structure:

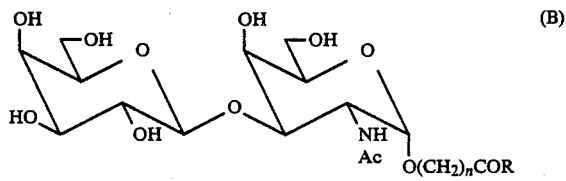

(B)

The bridging arm —O(CH$_2$)$_n$COR permits attachment, through an amide linkage of the carbonyl group, to a variety of insoluble or soluble aminated or amine-containing supports to yield artificial antigens and immunoadsorbents of the T-antigenic determinant. The bridging arm embodied in the present invention is 8-methoxycarbonyloctanol, however variations in the length of the alkyl chain or in the nature of the alkoxy group would be obvious to a skilled chemist and would not be expected to alter the utility of the above monosaccharide or disaccharide products of this invention.

It will be recognized that the abovedescribed processes produce the desired O-α-anomeric linkage with the bridging arm of the monosaccharide product, and the desired O-β-anomeric linkage between the two sugars of the disaccharide product. The use of the α-D-galactopyranosyl bromide as opposed to the β-D-galactopyranosyl chloride as the starting material is preferred since the former is simpler to prepare and yet offers the same yield of the desired products as does the β-D-galactopyranosyl chloride.

In arriving at the processes of the present invention it was found that the α,β ratios of the 2-azido glycosides formed vary unpredictably with not only the particular 2-azido-galactopyranosyl halide starting material, but also with the particular reaction conditions used and the particular alcohol being condensed with the halide. For instance, if the conditions of mercuric cyanide as a promotor with α-D-galactopyranosyl bromide are used, the undesired β-D-galactosaminide is formed in about 75% yield. If mercuric cyanide and mercuric bromide are used, again a 70–75% yield of the β-D-galactosaminide is obtained. Use of silver carbonate with catalytic silver trifluoramethanesulfonate as a promotor with 8-methoxycarbonyloctanol and either the β-D-galactopyranosyl chloride or the α-D-galactopyranosyl bromide, as reported in U.S. Pat. No. 4,195,174, leads to more of the β-glycoside than the α-glycoside. The silver carbonate, silver trifluoromethanesulphonate conditions can lead to the production of α-D-galactosaminides when the alcohol is a sugar, however these same conditions yield the undesired β-glycoside linkage when the alcohol is the aliphatic alcohol bridging arm.

In accordance with another aspect of the invention a method is provided for detecting a delayed type hypersensitivity reaction to the artificial T-antigen. The method comprises injecting intradermally in the human body the T-antigenic determinant (B) attached through an amide linkage of the carbonyl group of the bridging arm to a non-toxic soluble aminated or amine-containing antigen-forming carrier molecule, and thereafter observing a delayed type hypersensitivity reaction by the human body. The preferred artificial antigen is 8-methoxycarbonyloctyl-2-acetamido-2-deoxy-3-O-(β-D-galactopyranosyl)-α-D-galactopyranoside attached to human serum albumin. The amount of the T-antigenic determinant incorporated on the carrier molecule is preferably in the range of about 7 to 16 equivalents/mole.

DESCRIPTION OF THE PREFERRED EMBODIMENT

Figure 1:
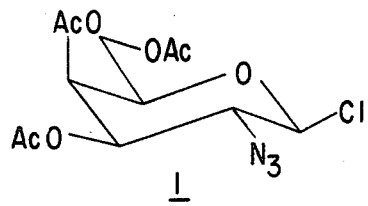
FIG. 1 is a formula sheet showing the structural formulas and names for compounds referred to by number in the specification.
Figure 1:
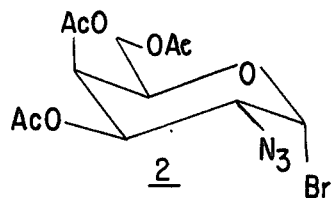
Figure 1:
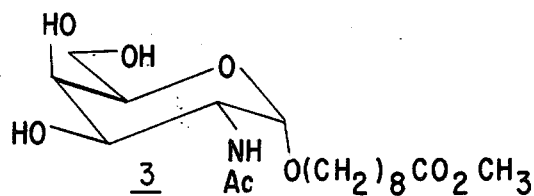
Figure 1:
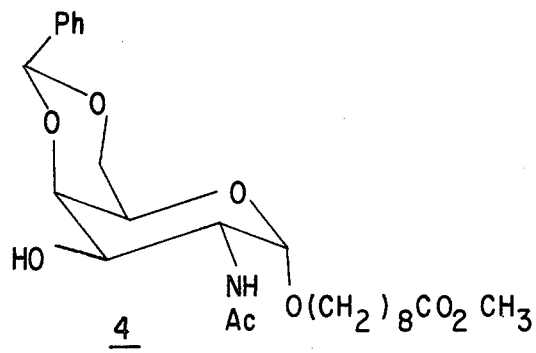
Figure 1:
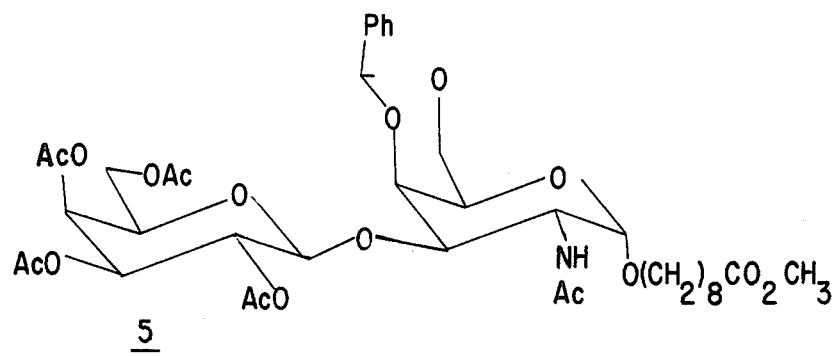
Figure 1:
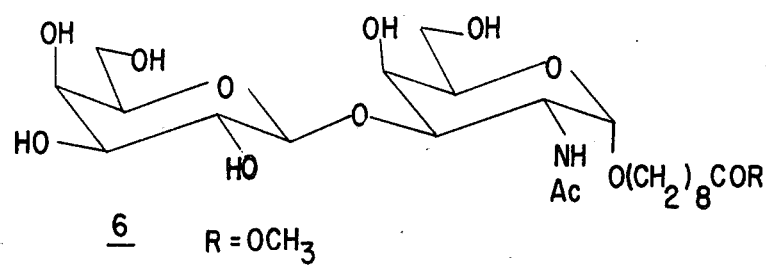

The first step in the process for the preparation of the desired T-antigenic determinant is to attach the monohydroxy carboxylate of the general formula HO(CH$_2$)$_n$COR, where n=3–9 and R is an alkoxy or aryloxy group to an O-acylated-2-azido-2-deoxy-D-galactopyranosyl halide with an α-D-anomeric linkage. In Example I herebelow, the particular 8-methoxycarbonyloctanol linking arm is α-linked to 3,4,6-tri-O-acetyl-2-azido-2-deoxy-β-D-galactopyranosyl chloride in the presence of mercuric cyanide promotor in a suitable solvent. In Example II herebelow, 8-methoxycarbonyloctanol is α-linked to 3,4,6-tri-O-acetyl-2-azido-2-deoxy-α-D-galactopyranosyl bromide in the presence of a halide ion source R$_4$'NBr where R' is a lower alkyl group, in a suitable solvent. In each case the O-α-glycoside formed by these reaction conditions is thereafter reduced and N-acetylated to convert the azide group to an acetamido group, and de-O-acylated to produce the O-α-glycoside having the structure:

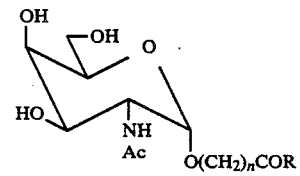

The de-O-acylation step may alternatively precede the reduction and N-acetylation step.

With the bridging arm 8-methoxycarbonyloctanol n=8 and R is a methoxy group. However, variations in the length of the aliphatic chain between about 3 and 19 will not significantly alter the bridging arm. The R group is selected from alkoxy and aryloxy protecting groups such as methoxy, ethoxy, propyloxy, butoxy and phenyloxy. In the above O-α-glycoside product, the initial R protecting group can be replaced, to facilitate coupling to a carrier or support. Suitable groups include NHNH$_2$, N$_3$ and OH.

The halide ion source R$_4$'NBr, used in Example II is tetraethylammonium bromide. Alternatives to the ethyl groups are lower alkyls such as ethyl, propyl or butyl groups.

In both Examples I and II the particular galactopyranosyl halide starting material is O-acetylated at the 3,4,6-O-hydroxy positions. Alternative protecting groups include acyl groups such as propionyl and benzoyl groups.

The solvent used in the abovedescribed processes is one which is capable of dissolving the starting materials at a level to provide sufficient concentration of these materials to react. The solvent is also selected to be substantially inert to the reaction taking place. The solvent used in Example I is dry benzenenitromethane. In Example II the solvent is dichloromethane. Alternative solvents having the abovedescribed properties will be evident to persons skilled in this art.

EXAMPLE I

8-Methoxycarbonyloctyl 2-acetamido-2-deoxy-α-D-galactopyranoside (3)

A solution of 3,4,5-tri-O-acetyl-2-azido-2-deoxy-β-D-galactopyranosyl chloride (14.0 g) in benzene (20 mL) was added to a mixture of 8-methoxycarbonyloctanol (8.46 g), mercuric cyanide (11.77 g), Drierite (42 g) and dry benzenenitromethane 1:1 (v/v) (225 mL). This mixture was stirred at 45° to 50° for 72 h, at which time the solids were removed by filtration through a Celite pad. The filtrate was concentrated to a syrup and dissolved in dichloromethane (200 mL). The resulting solution was washed with water (2×100 mL), dried, filtered, and concentrated to a syrup (17.8 g). Without further purification, this material was dissolved in acetic acid (50 mL) and hydrogenated at 100 psi at room temperature in the presence of 5% palladium on charcoal for 4 h. Acetic anhydride (2 mL) was added and the catalyst was removed by filtration. Reduction of the azido group may also be achieved with hydrogen sulfide in a basic solution or with metallic zinc. The filtrate was diluted with toluene and evaporated to a foam (17 g). Removal of the O-acetyl groups by transesterification using a catalytic amount of sodium methoxide in methanol (30 mL) followed by removal of the sodium ions with an acid resin and evaporation gave a foam (10.0 g). Crystallization from hot water provided pure 8-methoxycarbonyloctyl 2-acetamido-2-deoxy-α-D-galactopyranoside (3, 5.1 g) in an overall 35% yield, m.p. 138°–140°, $[\alpha]_D^{25}$+130.4° (c, 1.25, methanol); $^1$Hnmr (D$_2$O) δ: 4.95 (d, 1H, J$_{1,2}$=3.0 Hz, H-1), 2.12 (s, 3H, NAc); $^{13}$Cnmr (CH$_3$O$_D$) δ: 98.6 (C-1), 62.7 (C-6), 51.6 (C-2).

Anal. calcd. for C$_{18}$H$_{33}$N$_1$O$_8$·½H$_2$O: C, 53.98; H, 8.56; N, 3.50; found: C, 53.98; H, 8.31; N, 3.46.

8-Methoxycarbonyloctyl 2-acetamido-2-deoxy-β-D-galactopyranoside

The mother liquor from the above mentioned crystallization appeared to contain additional quantities of (3) along with an about 20% overall yield of the β-D-anomer. Consequently, the material was acetylated for chromatography on a silica gel column developed with hexane-ethyl-acetate-ethanol (6:4:1). The fraction which appeared to possess the β-anomer of O-acetylated (3) was de-O-acetylated in the usual manner using sodium methoxide in methanol. The product crystallized readily from methanoldiethyl ether, m.p. 178°–179.5°, $[\alpha]_D^{25}$−3.2° (c, 0.9, methanol); $^1$Hnmr (CD$_3$OD) δ: 4.40 (d, 1H, J$_{1,2}$=7.6 Hz, H-1), 2.01 (s, 3H, NAc); $^{13}$Cnmr (CD$_3$OD) δ: 102.9 (C-1), 62.3 (C-6), 54.2 (C-2).

Anal. calcd. for C$_{18}$H$_{33}$N$_1$O$_8$: C, 55.22; H, 8.50; N, 3.58; found: C, 55.44; H, 8.73; N, 3.62.

This compound is more readily prepared via the use of 3,4,6-tri-O-acetyl-2-azido-2-deoxy-α-D-galactopyranosyl bromide (2).

The α-bromide compound (2) may also be used to synthesize the α-glycoside (3). This is exemplified below.

EXAMPLE II

The α-bromide (2) (17.2 g) was stirred at ambient temperature with a mixture of 8-methoxycarbonyloctanol (16.0 g), tetraethylammonium bromide (9.6 g) and 4A° molecular sieves (60.0 g) in dichloromethane (75 mL) for 4 days. At that time the mixture was centrifuged to remove solids and the supernatant diluted with dichloromethane (400 mL) and washed with water (2×100 mL). Drying and evaporation of the organic layer gave s syrup (27.2 g). Treatment of this residue with metallic zinc (30.0 g) in acetic acid (75 mL) and acetic anhydride (25 mL) for 0.5 h, effected reduction of the azide and acetylation of the amine to provide the crude blocked α-D-galactosaminide. Dilution of the reaction mixture with dichloromethane (100 mL), filtration and evaporation gave a residue which was dissolved in dichloromethane (200 mL) and washed successively with water (50 mL), saturated sodium bicarbonate (100 mL) and water (2×100 mL). The organic layer was dried and evaporated to give syrup which was de-O-acetylated and crystallized as described above in Example I to provide 8-methoxycarbonyloctyl 2-acetamido-2-deoxy-α-D-galactopyranoside (3) (5.6 g).

In the next step of the process, the monosaccharidic O-α-glycoside is selectively blocked at the 4,6-O-hydroxyl positions to give a compound having the C-3 hydroxyl group as the only free hydroxyl group. The preferred blocking group is an acetal such as benzylidene. With the preferred bridging arm this step yields 8-methoxycarbonyloctyl-2-acetamido-4,6-O-benzylidene-2-deoxy-α-D-galactopyranoside (4).

EXAMPLE III

8-Methoxycarbonyloctyl 2-acetamido-4,6-O-benzylidene-2-deoxy-α-D-galactopyranoside (4)

Compound (3) (5.0 g) was dissolved in N,N-dimethylformamide (20 mL) containing α,α-dimethoxytoluene (8 mL) and p-toluenesulfonic acid (0.10 g). This mixture was heated to 50° for 5 h, at which time triethylamine (0.5 mL) was added and the solution was taken to dryness under vacuum to give an amorphous glass (5.2 g) which was extracted with pentane (2×50 mL). Crystallization of this solid from ethyl acetate-pentane gave the titled compound (4.5 g), m.p. 145°–146°, $[\alpha]_D^{25}$+101° (c, 1, chloroform); $^1$Hnmr (CDCl$_3$) δ: 5.74 (d, 1H, J$_{1,2}$=3.5 Hz, H-1), 2.02 (S, 3H, CH$_3$). $^{13}$Cnmr (CDCl$_3$) δ: 101.2 (CHPh), 98.6 (C-1), 62.9 (C-6), 50.5 (C-2).

Anal. calcd. for C$_{25}$H$_{37}$N$_1$O$_8$: C, 62.61; H, 7.78; N, 2.92; found C, 62.65; H, 7.75; N, 2.79.

In the final step of the synthesis of selectively blocked monosaccharide is reacted with a 2,3,4,6-tetra-O-acyl-α-D-galactopyranosyl halide in the presence of the promotor in a suitable solvent, to form a β-D-anomeric glycosidic linkage between the halide and the 3-hydroxyl group of the blocked glycoside. Subsequent removal of the O-protecting groups on both sugar yields the T-antigenic determinant hapten having the structure

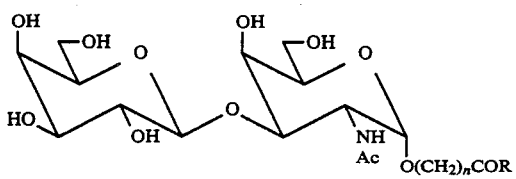

where n=3-19 and R is an alkoxy or aryloxy group.

The preferred acyl protecting groups on the galactopyranosyl halide are acetyl groups. The preferred promoter is mercuric cyanide, since it has been found effective in forming the desired O-β-glycosidic linkage with these particular reagents. The preferred solvent is dry benzene-nitromethane, however other inert solvents which will dissolve the starting materials to a sufficient extent, may be chosen.

EXAMPLE IV

The Synthesis of the T Antigenic Determinant Hapten 8-Methoxycarbonyloctyl 2-acetamido-2-deoxy-3-O-(β-D-galactopyranosyl)-α-D-galactopyranoside (6)

A solution of 2,3,5,6-tetra-O-acetyl-α-D-galactopyranosyl bromide (0.315 g) in benzene (2 mL) was added to a mixture of compound (4) (0.30 g), mercuric cyanide (0.18 g) anhydrous calcium sulfate (0.97 g) and dry benzene-nitromethane 1:1 (v/v) (50 mL). This mixture was stirred at 50° for 3 h, at which time another portion of the bromide (0.05 g) was added and the reaction was continued for an additional hour. The solids were removed and the filtrate was diluted with dichloromethane (100 mL), washed with water (2×50 mL) and dried. Solvent removal left a foamy product (5, 0.50 g) which resisted crystallization. The material was dissolved in dichloromethane (5 mL) and 90% aqueous trifloroacetic acid (1 mL) was added. (Aqueous acetic acid or hydrogenation can also be used for deprotection of the 4 and 6 hydroxyl groups.) After 2 min. at room temperature, toluene (5 mL) was added and then the solvent removed under vacuum at 30°. The residue was applied to a column (20×1.5 cm) of silica gel (40 g) which was eluted with benzene-ethyl acetate-ethanol (3:3:1). The main fraction provided a syrup (0.30 g) [$^{13}$Cnmr (CDCl$_3$): 97.7 (C-1), 101.7 (C-1')] which was de-O-acetylated with catalytic sodium methoxide in methanol followed by removal of the sodium ions with an acid resin. Filtration and evaporation gave a foam (0.175 g, 51% yield), which was one homogeneous spot by tlc developed with isopropanol-ammonium hydroxide-water (v/v) 7:1:2, and was crystallized from n-butanol-ethanol to give pure 8-methoxycarbonyloctyl 2-acetamido-2-deoxy-3-O-(β-D-galactopyranosyl)-α-D-galactopyranoside (6), m.p. 208°–210°, $[\alpha]_D^{25}$ +92.7° (c, 1.05, water); $^1$Hnmr (D$_2$O) δ: 4.91 (d, 1H, J$_{1,2}$ 3.5 Hz, H-1), 4.49 (d, 1H, J$_{1',2'}$ 6.25 Hz, H-1'), 2.05 (s, CH$_3$). $^{13}$Cnmr (CD$_3$OD) δ: 98.1 (C-1), 105.7 (C-1').

Anal. calcd. for C$_{24}$H$_{43}$N$_1$O$_{13}$.H$_2$0: C, 50.42; H, 7.93; N, 2.45. found: C, 50.62; H, 8.00; N, 2.53.

The activity of compound (6) as the T antigenic determinant was shown (a) by demonstrating inhibition of the natural T agglutinins with compound (6); (Example V) (b) by production of anti-T antibodies with an artificial T antigen (Examples VI and VII) (c) by preparation of an efficient T immunoadsorbent from compound (6) (Example VIII) and (d) by the preparation of T agglutinable erythrocytes by covalently coupling the T hapten to erythrocytes (Examples IX and X).

EXAMPLE V

Inhibition of human anti-T by compound (6)

The agglutination of neuraminidase treated O erythrocytes[20] by human anti-T (titre 1/32) was totally inhibited by compound (6) at a concentration of 1 mg/mL whereas methyl β-D-galactopyranoside and 8-methoxycarbonyloctyl 2-acetamido-2-deoxy-α-D-galactopyranoside (3) showed no inhibition at this concentration.

The utility of compound (6) for the preparation of artificial antigens was shown by attaching the disaccharide, through an amide linkage of the carbonyl group of the bridging arm, to a soluble carrier. In Example VI, compound (6) is converted to the acyl hydrazide by treatment with hydrazine hydrate and then attached by the previously described acyl azide coupling method[19] to soluble carriers to give artificial T-antigens. Suitable antigen forming carrier molecules are recognized, by persons skilled in the art, to be soluble, high molecular weight, aminated or naturally amine-containing compounds. Exemplary carriers include proteins, glycoproteins and polysaccharides.

EXAMPLE VI

Preparation of the 8-Hydrazinocarbonyloctyl 2-acetamido-2-deoxy-3-O-(β-D-galactopyranosyl)-α-D-galactopyranoside (7)

Compound (6) was dissolved in hydrazine hydrate and left to stand for 2 h. At that time, the solvent was removed by co-evaporation with butanol-water 1:1 (v/v) 3×5 mL) to provide the hydrazide (7) used in preparing artificial antigens and immunoadsorbents as described below.

EXAMPLE VII

Preparation of a Synthetic Antigen from 8-Hydrazinocarbonyloctyl 2-acetamido-2-deoxy-3-O-(β-D-galactopyranosyl-β-D-galactopyranoside (7)

A suspension of compound (7) (0.109 g) in dimethylformamide (1.5 mL) was cooled to near −20° C. under an inert atmosphere and to this was added dioxande 4.5N in HCl (186 μL) and tertiary-butyl nitrate (50 μL). The resulting solution was stirred while maintaining cooling for 2 h. At that time, the reaction was quenched by the addition of sulfamic acid (0.01 g), dissolved in dimethylformamide (0.408 mL) and stirring and cooling was continued for 15 min. This mixture was then added directly to a solution of human serum albumin (HSA) and 0.2N aqueous N-ethyldiethanolamine (36 mL, pH 9.03), cooled to 0°–4° C. After 20 h, this mixture was dialyzed against water to remove salts and unreacted reagents and lyophilized to provide the artificial antigen. A carbohydrate determination showed an incorporation of 13 hapten groups per HSA molecule.

The value of incorporation can be varied through a range from 6 to 30 by decreasing or increasing the amount of compound (7) used in relation to the amount of HSA used. Preferred hapten incorporation values range from about 7 to 16 equivalents/mole. Alternate buffers can be used such as a borate buffer, and alternate carrier molecules may be utilized.

Examples of antigens prepared are listed below:

| Antigen Designation | Carrier | Hapten Incorporation Equiv/mole (n) |
| --- | --- | --- |
| T-BSA | Bovine Serum Albumin | 22 |
| T-Hb | Horse Hemoglobin | 20 |
| T-HSA | Human Serum Albumin | 13 |
| T-IgG | Human Immunoglobulin G | 18 |

The utility of compound (6) for the preparation of an immunoabsorbent of the T-antigenic determinant is illustrated in Example VIII. The determinant is attached through an amide linkage of the carbonyl group of the bridging arm to an insoluble aminated or amine-containing immunoadsorbent-type support. The properties desirable in immunoadsorbent-type supports are well known in the art (see for example *Affinity Chromatography*, C. R. Lowe and P. D. G. Dean, John Wiley & Sons, London, 1974). Exemplary supports include derivatives of cellulose, polystyrene, synthetic poly-amino acids, crosslinked dextrans, polyacrylamide gels, porous glass and agarose.

EXAMPLE VIII

Preparation of an Effective Immunoadsorbent from 8-Hydrazinocarbonyloctyl 2-acetamido-2-deoxy-3-O-($\beta$-D-galactopyranosyl)-$\alpha$-D-galactopyranoside (7)

A solution of the acyl azide obtained from compound (7) (7.7 mg) in dimethylformamide (0.5 mL) as described in Example VI was added to a slurry of calcined diatomaceous earth (100–120) mesh, (20 g), which has been silylaminated[21], in acetonitrile (30 mL) at 4° C. After standing overnight, the solid was filtered and washed with methanol. N-acetylation of unreacted amines was achieved with acetic anhydride in methanol. Filtration and drying gave the T immunoadsorbent. Hapten incorporation was 0.3 M/g.

Human O sera (anti-T titre 1/32) adsorbed with 100 mg/mL of T immunoadsorbent showed after adsorption no anti-T activity.

EXAMPLE IX

Preparation of 8-Hydroxycarbonyloctyl 2-acetamido-2-deoxy-3-O-($\beta$-D-galactopyranosyl)-$\alpha$-D-galactopyranoside (8)

The ester compound (6) (0.17 g) was treated with 0.1N NaOH (4 mL) at room temperature for 2 h. The solution was then deionized with an acidic ion exchange resin and the solvent removed to provide the title acid (8).

EXAMPLE X

Preparation of T haptenized cells

One mL of packed red blood cells (type O Le$^{a+b-}$) was washed three times with fine volumes of buffer (0.01M N-ethyldiethanolamine, 0.15M NaCl, pH 6.0). Three-quarters of a mL of these washed cells was then suspended in 1.75 mL of the same buffer to give a 30% suspension, which was cooled in a 12×75 mm test tube. Acid derivative (8) (5 Mg) and 1-ethyl-3-(3'-dimethylaminopropyl)carbodiimide hydrochloride (3 Mg) were dissolved in 150 μL of 0.15M NaCl. This solution was held at room temperature for five minutes, and then added to the red blood cell suspension at 4° C. The reaction mixture was incubated at 4° C. with gentle rocking for two hours, and reagents removed by washing five times with five volumes of phosphate buffered saline.

Haptenization as confirmed by serological testing, which showed agglutination of the treated erythrocytes by human anti-T antibodies.

In the past the immune response has been considered to have two independent forms, one an antibody mediated response in which pathogens are neutralized by specific antibody molecules synthesized by the B lymphocytes and the other a cell mediated immunity based on the protective functions of thymus derived (T) lumphocytes. It is now known that this view is a gross oversimplification as it is apparent that there is a great deal of interaction between these branches of the immune system and that the adaptive reaction of an individual to an antigen challenge involves a complex network of interacting cells and soluble cell products. At present the understanding of the factors controlling this interaction is quite limited. With regard to delayed type hypersensitivity reactions, "a cell mediated" response, it is known that for a given hapten many factors such as carrier type and hapten incorporation will determine in an as yet unpredictable manner if a hapten specific DTH reaction will take place[22].

In the case of the T antigen it has been observed that although any healthy individuals possess anti-T agglutinins in their sera they have in general no DTH reactions to intradermal injection of T antigen[11]. In contrast individuals with certain forms of carcinoma particularly breast carcinoma will show a DTH reaction to T antigen[11]. Thus this reaction to the natural T antigen is strongly indicative of the presence of carcinoma and is of great diagnostic significance. Evidence in individuals with diagnosed cancer for DTH reactions to a product of the present invention, an artificial T antigen, T HSA, is presented below.

EXAMPLE XI

Demonstration of Delayed Type Hypersensitivity DTH to a T-HSA artificial antigen in Patients with Metastatic Breast Tumors Patients The study group (23 patients) was comprised of postoperative stage IV metastatic breast cancer patients currently under treatment at the W. W. Cross Cancer Institute, Edmonton, Alberta, Canada. Informed consent was obtained from all the individuals who volunteered to participate in this study.

Antigens

Conjugates of human serum albumin (HSA) with the T hapten were prepared under aseptic conditions as described above. For use in the human body, the antigen-forming carrier molecule should be non-toxic. Four different incorporations n=7, 12, 14 and 22 were examined. The HSA used was prepared by Cohn fractionation of human plasma in accordance with the requirements of the U.S. Food and Drug Administration. All patients also received HSA, which was processed as described for the preparation of T-HSA antigen except that no hapten was used in the reaction mixture.

Administration of the Antigen

Both T-HSA and HSA were injected intradermally in separate sites on the upper arm in a total volume of 0.1 mL saline. Antigen concentrations were 100 and 200 Mg/mL (10 and 20 mg of antigen per injection).

Delayed Type Hypersensitivity Reactions

A positive reaction was taken as erythema, with or without induration, of greater than 5 mm diameter at 24 h. Where doubt existed weight was given to induration. Positive responses to T-HSA varied from 8 to 20 mm. In some cases positivity to T-HSA was confirmed by skin punch biopsies which showed perivascular lymphocyte infiltration.

Results

Of the patients tested none showed positively to HSA and 16 (70%) showed a DTH reaction to T-HSA (n=12 or 14). Of the patients giving a positive reaction the response was greater at the highest antigen concentration. The DTH response was also effected by hapten incorporation with the greatest response being to antigens with 'n' values being between 12 and 14. Those patients not responding to T-HSA were found to have recently undergone (within 3 months) various therapy programs and thereby possibly rendered anergic to the T antigen. Such patients were excluded from the study in its later stages.

While the present invention has been disclosed in connection with the preferred embodiment thereof, it should be understood that there may be other embodiments which fall within the spirit and scope of the invention as defined by the following claims.

References

1. O. Thomsen, Z. Immun.-Forsch., 52 (1927) 85–107.
2. V. Friedenreich, *The Thomsen Hemagglutination Phenomenon*, Levin & Munksgaard, Copenhagen (1930).
3. C. M. Chu, Nature, 161 (1948) 606–607.
4. Z. Kim and G. Uhlenbruck, Z. Immun.-Forsch., 130 (1966) 88–99.
5. R. R. Race and R. Sanger, Blood Groups in Men, 6th ed., Blackwell Scientific Publications, Oxford (1978) 486–487.
6. P. Vaith and G. Uhlenbruck, Z. Immun.-Forsch., 154 (1978) 1–14.
7. P. J. Klein, R. A. Newman, P. Muller, G. Uhlenbruck, H. E. Schaefer, K. J. Lennartz and R. Fischer, Klin, Wschr., 56 (1978) 761–765.
8. D. R. Howard, Vox. Sang., 37 (1979) 107–110.
9. R. A. Newman, P. J. Klein and P. S. Rudland, JNCI 63, (1979) 1339–1346.
10. J. H. Anglin, Jr., M. P. Lerner and R. E. Nordquist, Nature, 269 (1977) 254–255.
11. G. F. Springer, P. R. Desai, M. S. Murthy, H. Tegtmeyer and E. F. Sanlon, Prog. Allergy, 26 (1979) 42–96 and references contained therein.
12. Y. D. Kim, U.S. Pat. No. 4,241,044.
13. G. F. Springer and P. R. Desai, Carbohyd. Res., 40 (1975) 183–192.
14. R. Kaifu and T. Osawa, Carbohyd. Res., 69 (1979) 79–88.
15. R. U. Lemieux, D. R. Bundle and D. A. Baker, U.S. Pat. No. 4,137,401.
16. R. U. Lemieux, D. A. Baker and D. R. Bundle, Can. J. Biochem., 55 (1977) 507–512.
17. H. Paulsen, C. Kolar and W. Stenzel, Angew. Chem. Int. Ed., 15 (1976) 440–441.
18. R. U. Lemieux and R. M. Ratcliffe, U.S. Pat. No. 4,195,174.
19. R. U. Lemieux, D. R. Bundle and D. A. Baker, J. Amer. Chem. Soc., 97 (1975) 4076–4083.
20. H. H. Sunson, F. Stratton and G. W. Mullard, Brit. J. Haematol., 18 (1970) 309–316.
21. H. H. Weetall in *Methods in Enzymology*, Vol. XLIV, Ed. K. Mosbach, Academic Press, New York, 1976, p. 140.
22. V. E. Jones and S. Leskowitz, Nature, 207 (1965) 596–597.

The embodiments of the invention in which an exclusive property or privilege is claimed are defined as follows:

1. The human T-antigenic determinant hapten having the structure

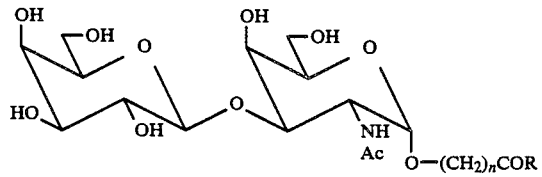

where n=3–19, and R is an alkoxy, aryloxy, $NHNH_2$, OH or $N_3$ group.

2. The human T-antigenic determinant hapten of claim 1 characterized as 8-methoxycarbonyloctyl-2-acetamido-2-deoxy-3-O-(β-D-galactopyranosyl)-α-D-galactopyranoside.

3. A composition comprising the hapten of claim 1 wherein the $(CH_2)_n COR$ is alpha o-glycosidically linked to the T disaccharide, essentially free of the beta anomer.

4. The composition of claim 3 wherein n=8 and R is a methoxy group.

* * * * *